United States Patent [19]

Schrider et al.

[11] 3,978,168

[45] Aug. 31, 1976

[54] O,O,O',O'-TETRAMETHYL O,O'-TRITHIODI-P-PHENYLENE ESTER

[75] Inventors: Michael Stanley Schrider, South Bound Brook; Stephen David Levy, Trenton, both of N.J.

[73] Assignee: American Cyanamid Company, Stamford, Conn.

[22] Filed: Apr. 21, 1975

[21] Appl. No.: 570,293

[52] U.S. Cl.............................. 260/930; 260/973; 424/206
[51] Int. Cl.² ...................... C07C 9/06; A01N 9/36
[58] Field of Search ................................... 260/930

[56] References Cited

UNITED STATES PATENTS 3,493,655    2/1970    Magee ............................ 260/930 X

*Primary Examiner*—Anton H. Sutto
*Attorney, Agent, or Firm*—Denis A. Polyn

[57] ABSTRACT

This invention relates to phosphorothioic acid, O,O,O',O'-tetramethyl O,O'-trithiodi-p-phenylene ester and its use in controlling insects and acarina in warm-blooded animals.

1 Claim, No Drawings

O,O,O',O'-TETRAMETHYL O,O'-TRITHIODI-P-PHENYLENE ESTER

SUMMARY OF THE INVENTION

This invention relates to phosphorothioic acid, O,O,O',O'-tetramethyl O,O'-trithiodi-p-phenylene ester useful for controlling acarina, particularly as a pesticide to control ticks on cats and dogs.

The active component of the present invention can be illustrated by the following structure:

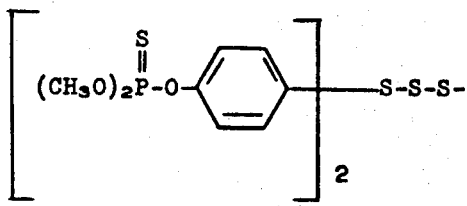

The compound phosphorothioic acid, O,O,O',O'-tetramethyl O,O'-trithiodi-p-phenylene ester may be prepared by reacting the diphenol:

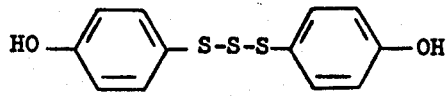

with at least 2 moles of O,O-dimethyl phosphorohalidothioate represented by the formula:

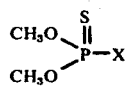

wherein X is halogen, preferably chlorine.

The reaction between the diphenol and the O,O-dimethyl phosphorohalidothioate is carried out on a relative mole basis of one mole of the diphenol to at least 2 moles of the phosphorohalidothioate, although up to 4 moles of the phosphorohalidothioate may be employed to advantage, under alkaline conditions and in the presence of a polar solvent such as water, methyl ethyl ketone, and the like, at a temperature of from between 0°C. and 100°C. This compound may also be prepared in solvents having a wide range of polarity employing a variety of methods to prevent the accumulation of hydrogen halide by-product.

We have now found that the compound phosphorothioic acid, O,O,O',O'-tetramethyl O,O'-trithiodi-p-phenylene ester is highly effective topically and systemically in controlling ticks.

The use of phosophorothioic acid, O,O,O',O'-tetramethyl O,O'-thithiodi-p-phenylene ester to control the infestation or reinfestation of dogs and cats by ticks is a novel use of this material. The use of the aforementioned compound to control insect pests, particularly ticks on dogs and cats is novel.

It is known that O,O-diethyl O-(2-isopropyl-6-methyl-4-pyrimidiny)phosphotothiate (Diazinon) and O,O-dimethyl S-(1,2-dicarbethoxyethyl)dithiophosphate (Malathion) are among the insecticides currently used as sprays to control lice on cattle, but is it usually recommended that two applications of these materials be made within a few weeks of each other. The use of O,O-diethyl O-(3,5,6-trichloro-2-pyridyl)phosphorothioate (Dursban chloropyrifos) has been reported by Buchanan et al., *New Zealand Vet. Journal* 19 (9) : 197–202 (1971), to give effective control of lice on cattle with single spray treatment.

The control of infestations of ticks or reinfestations of the same, is most desirable because of the economic losses caused by these pests.

Among the ectoparasites are included acarina such as Boophilus, Amblyomma, Anocentor, Dermacentor, Ixodes, Haemaphysalis, Hyalomma, Rhipicentor, Morgaropus, Rhipicephalus, Argas, Otobius and Ornithodoros, in the larval, nymph and adult stages, and the compound of this invention is particularly useful to control the cattle tick, *Boophilus microplus*.

The use of phosphorothioic acid, O,O,O',O'-tetramethyl O,O'-trithiodi-p-phenylene ester to control ticks on warm-blooded animals is particularly advantageous because it is substantially non-toxic at concentrations many times that of the actual amounts employed. The active ingredient, phosphorothioic acid, O,O,O',O'-tetramethyl O,O'-trithiodi-p-phenylene ester may be conveniently formulated as dusts, dust concentrates, wettable powders, emulsifiable concentrates, PVC collers and as solutions, with conventional solid or liquid adjuvants. It may also be incorporated in feed or in animal treat which is highly palatable to the animal. Wettable powders and emulsifiable concentrates are particularly useful since they can be diluted with water and applied topically as dilute liquid sprays to the animals which are to be protected from attack. In the latter situation, the dilute liquid formulations may also be used as dips as well as sprays.

Dusts or dust concentrates can be prepared by grinding together the inert solid diluent such as attapulgite, kaolin, walnut shell flour, diatomaceous earth, ground corn cob grits, or ground coconut shell, and the active ingredient, where such active ingredient is in solid form. Where the active ingredient is liquid, it may be sprayed on the carrier and thoroughly mixed with it or it may be dissolved in a solvent such as acetone, xylene, lard or vegetable oils and the solution sprayed on the solid carrier. Dusts usually contain from about 1% to 15% by weight of active ingredient, whereas concentrates may contain from about 16% to about 85% by weight of the active material.

Solutions in organic solvents such as various ketones, lower monohydric aliphatic alcohols, ketoalcohols such as diacetone alcohol, various esters, aromatic and aliphatic hydrocarbons may be applied as a spray or pour-on.

Wettable powders are prepared in the same fashion as dust concentrates, except that about 5% to 10% by weight of a surfactant, and 5% to 10% of a dispersing agent are included therein.

The active component of the present invention may also be prepared as emulsifiable concentrates by dissolving or dispersing about 10% to 75% by weight of the active compound in a suitable solvent or carrier such as a petroleum distillate having minimum aromatic content of 85% and admixing therewith about 10% by weight of an emulsifier such as polyoxyethylene derivatives and blends with alkyl aryl sulfonates. These concentrates are also generally dispersed in water or other suitable solvent for application.

The application is preferably made at a dose concentration which is lethal for adult insects and acarina, and provides ultimate control of said pests through ovicidal or larvicidal activity.

Application of the active ingredient can be made either directly, as by dusting, dipping and spraying, or by pour-on, or from pressure spray cans.

As an ovicidal agent, an application of about 0.1 mg. to 140 mg./kg. of the active ingredient is effective for preventing embryogenesis of insect and acarina ova. Preferably, the rate of application should be from 1 to 100 mg./kg.

As a larvicidal agent, we have found that generally about 0.001% to 1.0% of the compound phosphorothioic acid, 0,0,0',0'-tetramethyl 0,0'trithiodi-p-phenylene ester is effective for controlling *Boophilus microplus* larvae. Preferably, the rate of application to larvae ranges from about 0.001% to 0.4%.

The compound phosphorothioic acid, 0,0,0',0'-tetramethyl 0,0'-trithiodi-p-phenylene ester can be administered to warm-blooded animals such as dogs and cats in from 0.5 to 400 mg./kg. of body weight in a physiologically acceptable diluent, including cat and dog food, gelatin and the like.

In practice, the feed containing the anti tick compound should provide the animal with from 3 to 50 mg./kg./day of said compound for long term feeding, for example, for from several weeks to several months or continuously. Diets providing from 50 to 400 mg./kg./day will generally be administered for periods of short duration, i.e., 1 to 10 days. Weights given as mg./kg./day means mg./kg. of animal body weight per day.

It is of course obvious that the active compound may also be administered orally in the form of a pill, tablet, capsule or oral liquid using traditional carriers and excipients. Dosages should provide the mg./kg./day requirements given above with respect to administration in the feed.

SPECIFIC DISCLOSURE

The present invention is illustrated by the following example. All parts and percentages are by weight unless otherwise specifically designated.

EXAMPLE 1

Preparation of Phenol, 4,4'-trithiodi-

A solution of 80 parts by weight of phenol in 156 parts by weight of toluene is cooled to −2° to +4°C and a solution of 35 parts by weight of sulfur dichloride in 52 parts by weight of toluene is added thereto over a 3-hour period while keeping the temperature at −3° to +2°C. On completion of the addition, the solution is stirred for about 15 hours and allowed to reach room temperature. The solution is then warmed to 30°C and subjected to reduced pressure to remove residual hydrogen chloride gas. The toluene solution is then washed successively with water, 5% sodium carbonate and water. Concentration of the toluene phase gives a crystalline solid which on recrystallization from benzene melts at 147°–149°C. Anal. calcd. for $C_{12}H_{10}S_3O_2$ (in percent): C, 51.04; H, 3.57; S, 34.06. Found: C, 50.99; H, 3.51; S, 34.02.

EXAMPLE 2

Preparation of Phosphorothioic acid, 0,0,0',0'-Tetramethyl 0,0'-Trithiodi-p-phenylene Ester A solution of 0.05 mole of 4,4'-trithiodiphenol (Example 1) in tertiary butanol is treated with 0.10 mole of potassium tertiary butoxide and 0.10 mole of 0,0-dimethyl-phosphorochloridothioate for 2 hours at room temperature and then heated for 30 minutes at 60°C. The solids are filtered and the filtrate is partitioned between water and chloroform. The chloroform phase is washed successively with 5% sodium carbonate solution and water and then concentrated under reduced pressure to obtain a 75% yield of crude residue. Chromatography of the residue gives a yellow oil $N_D^{25} = 1.6185$. Anal. calcd. for $C_{16}H_{20}O_6P_2S_5$ (in percent): C, 36.22; H, 3.80; P, 11.68; S, 30.21. Found: C, 36.20; H, 3.87; P, 11.67; S, 30.22.

EXAMPLE 3

Acaricidal Activity

Effective control of unfed nymphs of the species *Amblyomma americanum* (lone star tick) is demonstrated in a test in which the nymphs are sprayed for 30 seconds with an acetone/water solution containing 10.0 and 3.3 ppm, respectively, of the test compound. Each test group contained 10 nymphs and all tests are replicated. After treatment the ticks are held for 48 hours at room temperature and 80% relative humidity. The results are reported in the following Table as percentage of the group killed.

TABLE

| Compound | Test Rate | Mortality (%) |
|---|---|---|
| 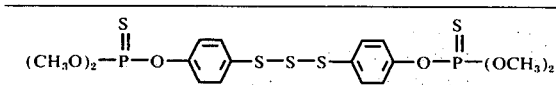 | 10.0 ppm<br>3.3 ppm | 90<br>10 |

EXAMPLE 4

Larvicidal Activity

Effective control of Acarina larvae is demonstrated in the following test with larvae of *Boophilus microplus* using a 10% acetone/90% water mixture containing 100 ppm of test compound. Twenty larvae are enclosed in a pipet sealed at one end with a gauze material and solution containing the test compound is then drawn through the pipet with a vacuum hose simulating a spray system. The treated ticks are then held for 48 hours at room temperature and 80% relative humidity and percent mortality is determined.

The compound, phosphorothioic acid, 0,0,0',0'-tetramethyl 0,0'-trithiodi-p-phenylene ester, is 100% effective against the larvae of *Boophilus microplus* at a concentration of 100 parts per million.

We claim:

1. The compound phosphorothioic acid, 0,0,0',0'-tetramethyl 0,0'-trithiodi-p-phenylene ester.

* * * * *